(12) United States Patent
Lee

(10) Patent No.: US 8,200,277 B2
(45) Date of Patent: Jun. 12, 2012

(54) MOBILE PHONE WITH A STETHOSCOPE

(76) Inventor: Byung Hoon Lee, Seoul (KR)

(*) Notice: Subject to any disclaimer, the term of this patent is extended or adjusted under 35 U.S.C. 154(b) by 965 days.

(21) Appl. No.: 11/885,108

(22) PCT Filed: Nov. 10, 2005

(86) PCT No.: PCT/KR2005/003800
§ 371 (c)(1),
(2), (4) Date: Aug. 23, 2007

(87) PCT Pub. No.: WO2006/090964
PCT Pub. Date: Aug. 31, 2006

(65) Prior Publication Data
US 2008/0146276 A1    Jun. 19, 2008

(30) Foreign Application Priority Data

Feb. 25, 2005  (KR) .................. 20-2005-0005158 U
Feb. 25, 2005  (KR) .................. 20-2005-0005178 U

(51) Int. Cl.
*H04M 1/00*  (2006.01)
(52) U.S. Cl. ............ 455/556.1; 455/557; 600/586; 600/573; 600/300; 381/67
(58) Field of Classification Search ....... 455/556.1–557; 600/586, 573, 300; 381/67
See application file for complete search history.

(56) References Cited

U.S. PATENT DOCUMENTS

| | | | |
|---|---|---|---|
| 5,737,429 A | 4/1998 | Lee | |
| 6,520,924 B2 * | 2/2003 | Lee | 600/586 |
| 6,790,178 B1 * | 9/2004 | Mault et al. | 600/300 |
| 7,115,102 B2 * | 10/2006 | Abbruscato | 600/586 |
| 2001/0050720 A1 * | 12/2001 | Karube et al. | 348/373 |
| 2002/0058889 A1 * | 5/2002 | Lee | 600/586 |
| 2002/0188227 A1 * | 12/2002 | Chong et al. | 600/586 |
| 2004/0078219 A1 * | 4/2004 | Kaylor et al. | 705/2 |
| 2004/0109571 A1 * | 6/2004 | Yoshimine | 381/67 |
| 2004/0157612 A1 * | 8/2004 | Kim | 455/445 |

(Continued)

FOREIGN PATENT DOCUMENTS

KR    10-0387201    5/2002

(Continued)

OTHER PUBLICATIONS

Korean Intellectual Property Office, International Search Report, PCT/KR2005/003800, Feb. 27, 2006, 2 pages.

*Primary Examiner* — Fayyaz Alam
(74) *Attorney, Agent, or Firm* — J. Bennett Mullinax, LLC

(57) ABSTRACT

Disclosed herein is a mobile phone with a stethoscopic function. The mobile phone with a stethoscopic function, of which the mobile phone has communication data processing functions, comprises a stethoscopic microphone which is arranged in a body of the mobile phone; and a stethoscopic system which is embedded in the body of the mobile phone. The auscultated sound data obtained from the medical examination made on the part of a human body where the stethoscopic microphone is contacted are converted into digital auscultated sound data. The digital auscultated sound data identifies corresponding sound data in the pre-stored standardized digital auscultating sound data through search and comparison within allowable errors of data. With the identified data, a diagnostic data is made available. The diagnostic data may be stored and transmitted to a physician using the communication function of the mobile phone.

15 Claims, 5 Drawing Sheets

U.S. PATENT DOCUMENTS

| | | | |
|---|---|---|---|
| 2005/0124375 A1* | 6/2005 | Nowosielski | 455/550.1 |
| 2005/0157887 A1* | 7/2005 | Kim | 381/67 |
| 2006/0169529 A1* | 8/2006 | Tamakoshi | 181/131 |
| 2007/0213613 A1* | 9/2007 | Ishida et al. | 600/439 |
| 2008/0269571 A1* | 10/2008 | Brown et al. | 600/300 |
| 2008/0298603 A1* | 12/2008 | Smith | 381/67 |
| 2009/0105605 A1* | 4/2009 | Abreu | 600/549 |
| 2010/0016918 A1* | 1/2010 | Mann et al. | 607/23 |
| 2010/0035580 A1* | 2/2010 | Wesby-Van Swaay | 455/411 |

FOREIGN PATENT DOCUMENTS

| | | |
|---|---|---|
| KR | 10-2002-0095004 | 12/2002 |
| KR | 10-2003-0018702 | 3/2003 |
| KR | 2004-0042273 | 5/2004 |
| WO | WO/2006/090964 A1 | 8/2006 |

* cited by examiner

[Fig. 1]
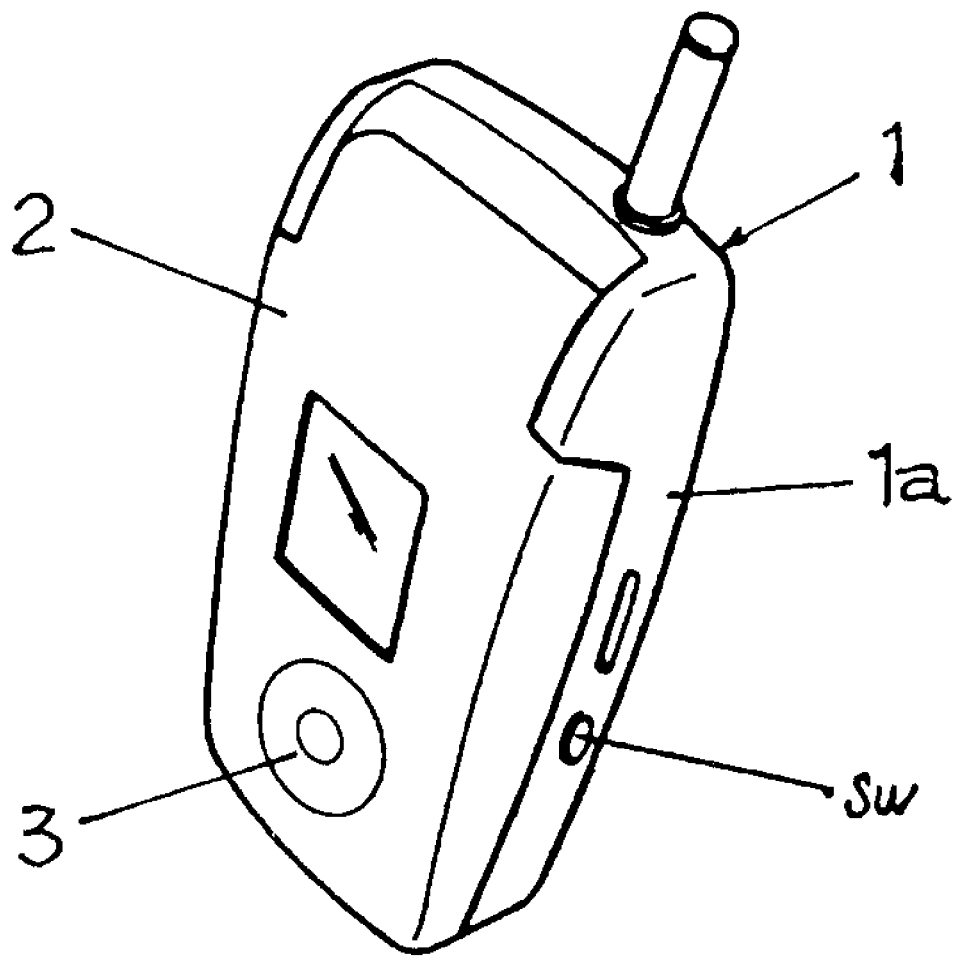

[Fig. 2]
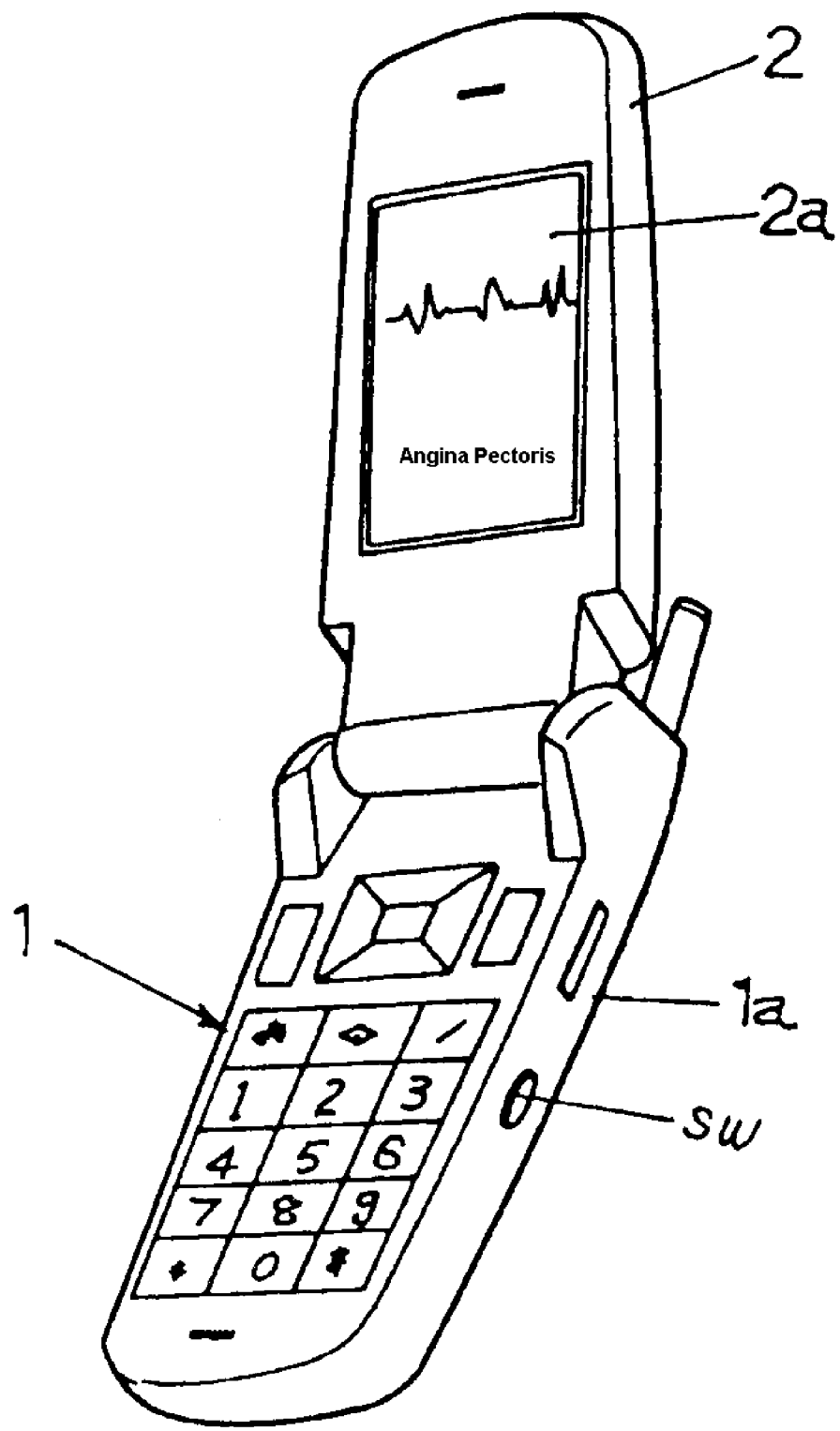

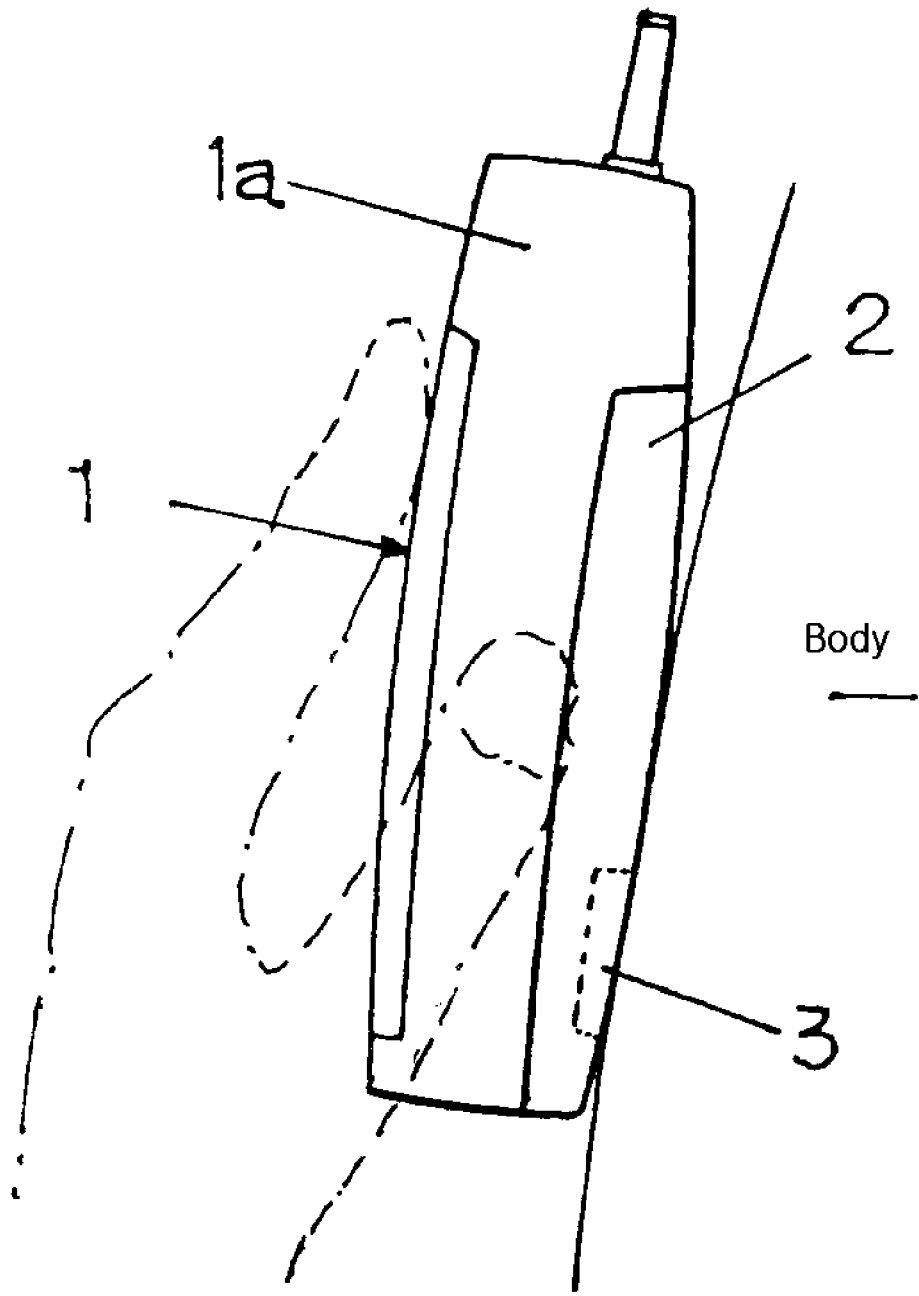
[Fig. 3]

[Fig. 4]
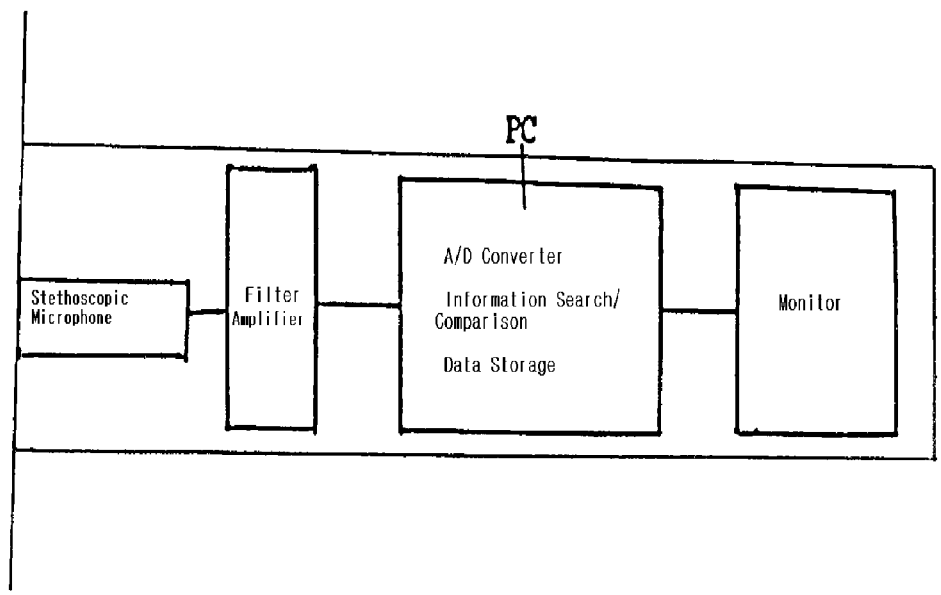
[Fig. 5]
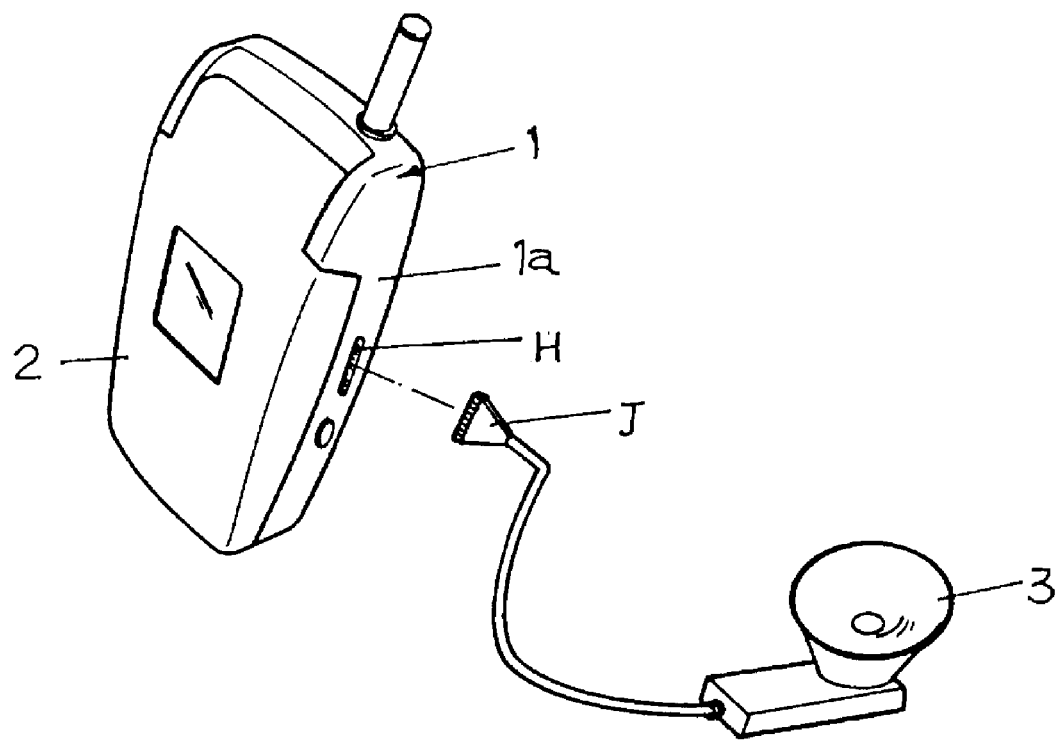

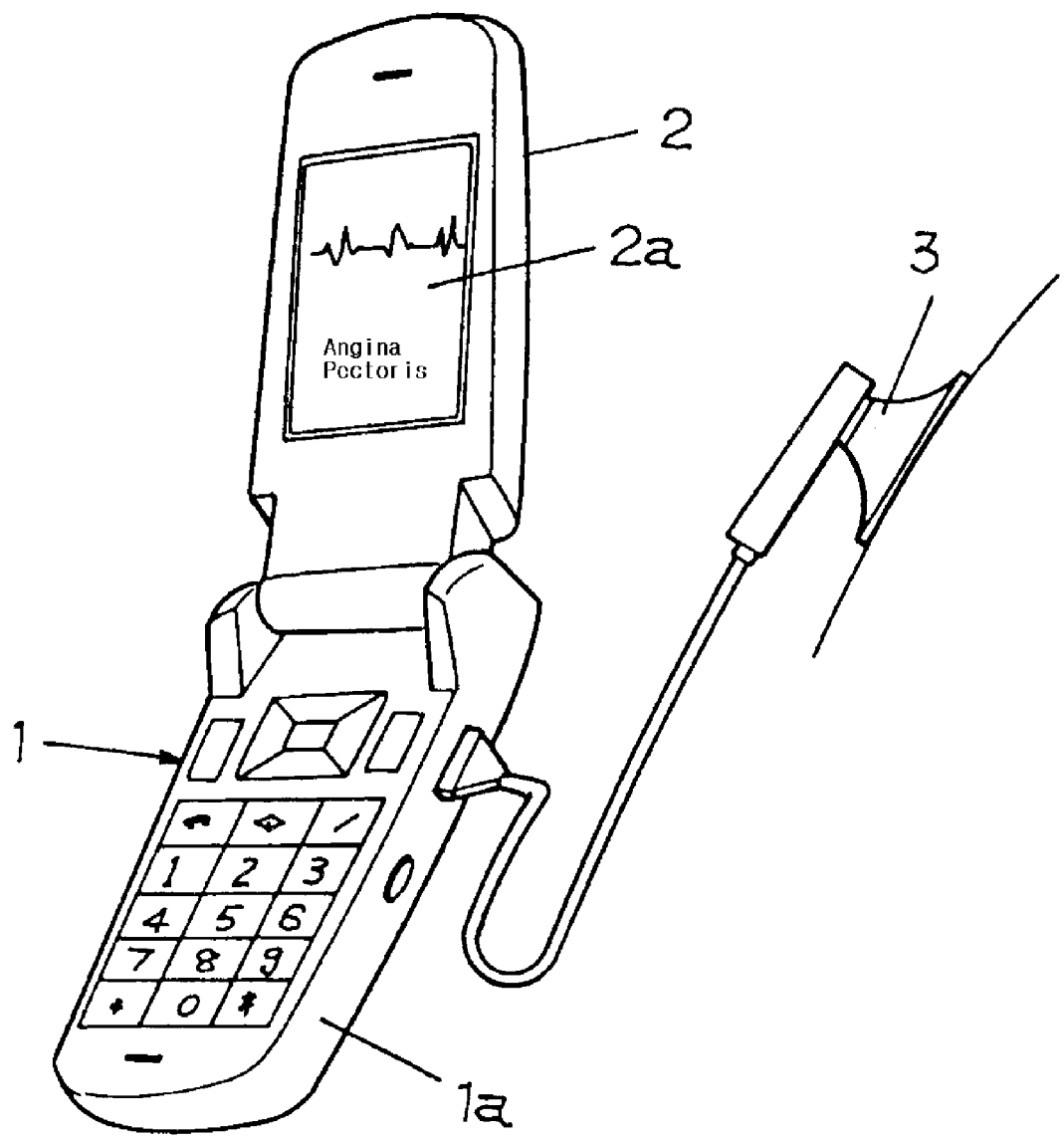
[Fig. 6]

MOBILE PHONE WITH A STETHOSCOPE

RELATED APPLICATIONS

This application claims the benefit of Korean Patent Application No. 20-2005-0005158 filed on Feb. 25, 2005 and Korean Patent Application No. 20-2005-0005178 filed on Feb. 25, 2005. The entire contents of Korean Patent Application Nos. 20-2005-0005158 and 20-2005-0005178 are incorporated by reference herein in their entireties for all purposes.

TECHNICAL FIELD

The present invention relates to a mobile phone with a stethoscope, and more particularly to a mobile phone with a stethoscope wherein a stethoscopic function is incorporated into a mobile phone with a function of wireless communication and data processing, the stethoscopic function producing diagnostic data.

BACKGROUND ART

In general, when a physician examines a patient, the first step is to identify the illness of a patient using a stethoscope in order to pinpoint the name of the patient's illness by the auscultated sound from the stethoscope. According to the diagnosis thus made with a stethoscope, a diagnostic plan for the patient is formulated. Depending upon the result of the initial diagnosis, further diagnostic procedure may be taken with higher precision diagnostic equipment.

Therefore, the first diagnostic step by means of a stethoscope is very important since it sets the course of the treatment for the patient. However, people living in modern times, accustomed to science and technology, tend to rely more on the results obtained from mechanical or electronic apparatus than on the diagnosis performed by the intuition and skill of an experienced physician.

Moreover, there can be a degree of difference between physicians in their diagnosis by a stethoscope through the auscultated sound, and the patient is not ready to accept such a diagnostic difference between physicians or between hospitals even if it is a minor difference. As a result, the patient is often exposed to an uncomfortable situation of accepting or rejecting without confidence the diagnosis made by the physician and the hospital.

In order to solve the above problem, an invention was disclosed in a prior art, in which the auscultated sound from a stethoscope automatically produces a diagnosis of a patient's illness on a display monitor through computer circuits without resort to a physician's intuition and experience.

According to said prior art, [Korean Patent Gazette 10-0387201 (published dated 12 Dec. 2003) and U.S. Pat. No. 6,520,924 B2 (registered dated 18 Feb. 2003) and U.S. Pat. No. 5,737,429], which were issued to the same inventor of the present application, analog wave signals of the auscultated sound data collected from an auscultating microphone of a stethoscope are converted into digital signals by an A/D converter, and then the converted digital signals are compared through searches with various standardized digital auscultating sound data of various symptoms of various illnesses which are stored by symptom of illness in computer circuits of a diagnostic system. By doing so, the auscultated sound data converted into digital auscultated sound data identifies the symptom of the patient's illness in the standardized diagnostic sound data stored in the computer circuits of a diagnostic system. In this process, the identification of the illness is done within allowable errors of data. The identified data showing the result of the diagnosis of the patient's illness is displayed on a monitor in visible characters showing the name of an illness, waveforms, pictures, and audible sounds.

This method of electronic diagnosis may resolve the problem of minor differences in diagnosis between physicians because the same diagnosis is available for the same symptoms of illness. This induces a patient to trust the physician and the diagnosis and helps lead to the enhancement of the results of the treatment.

DISCLOSURE OF INVENTION

Technical Problem

The invention of the present application is made to resolve the above-noted problem by providing a mobile phone equipped with a stethoscopic function by which a person can provide the physician at a hospital with a diagnostic data obtained through self-diagnosis by means of a mobile communication system without visiting the doctor or the hospital.

Mobile phones are in such a huge demand and supply that the majority of people in nearly every country have a mobile phone. The mobile phone as a means of mobile communication has its own function of a portable telephone which transmits a sound wave using a high frequency carrier wave and enables the user to communicate with a remote correspondent wireless.

With the development of the integrated circuit (IC) and the image display monitor, the mobile phone can be produced in a compact size. The compact-size mobile phone can house computer circuits to perform versatile functions including the connection to the Internet, data processing for various operations of data and transmission of music data, characters, moving images, and so forth.

Despite the fact that the mobile phone has communication circuits and data processing circuits capable of performing various operations, a mobile phone with a stethoscope has not been disclosed to date.

Technical Solution

The present invention has been made combining stethoscopic system stored in a small computer chip as used in the "Automatic Diagnostic Apparatus with a Stethoscope" of the aforesaid Korean Patent Gazette No. 10-0387201, an invention by the same applicant with that of the present application, with a communication function of an ordinary mobile phone provided with data processing circuits. With this combination, the apparatus enables a person to do a self-diagnosis without visiting a hospital, using the means of communication of a mobile phone equipped with a stethoscopic function and outputting and transmitting to the hospital at a long distance the diagnostic data displayed on the monitor visually and audibly In accordance with an aspect of the present invention, the above and other objects can be accomplished by the provision of a mobile phone with a stethoscope of which the mobile phone is provided with a display monitor and a communication function, the mobile phone with a stethoscope comprising: a small-sized high-performance stethoscopic microphone being arranged within or outside a body of the mobile phone; an operating switch for operating a stethoscopic system, which is arranged at a side of the body; and a stethoscopic system embedded as a customized chip in the body of the mobile phone, said stethoscopic system comprising: a filter unit for filtering noises mixed with an auscultated sound; an amplifier unit for amplifying the auscultated sound; an A/D converter unit for converting analog wave data of the auscultated sound into digital auscultated sound data; an auscultating sound storage unit for storing standardized digital auscultating sound data; an information search and comparison unit for comparing the digital auscultated sound data with the standardized auscultating sound data stored in the auscultating sound storage to identify the illness by name; a storage unit for storing the diagnostic data as a result of search and comparison; and an output unit for outputting the diagnostic data.

The stethoscopic microphone according to the present invention may either be an interior stethoscopic microphone which is embedded in a cover of the mobile phone, or an exterior stethoscopic microphone which is detachable from the body of the mobile phone, and either the interior or the exterior stethoscopic microphone is connected to the stethoscopic system which are stored in a customized chip and embedded in the body of the mobile phone.

When a user wants to auscultate, he or she makes the mobile phone with a stethoscope contact where the auscultation is to be made, namely, the place where the medical examination is to be made on a human body. The analog wave data of the auscultated sound are collected by the stethoscopic microphone, and then they are filtered by the filter unit since they contain contact sounds and various other noises, for contact sounds are generated when the stethoscopic microphone is contacted onto the human body, and various noises are absorbed from the surroundings. Next, the analog auscultated sound data are amplified by the amplifier, and then they are converted into digital auscultated sound data by the A/D converter. When the converted digital auscultated sound data are inputted into the search/comparison unit, they do a search and comparison operation against the pre-stored standardized digital auscultating sound data by symptom of illness. If the converted digital auscultated sound data identifies its equivalent in the pre-stored standardized auscultating sound data stored by symptom of illness within the allowable errors, the identified data, namely diagnostic data, are outputted through the output unit. The outputted diagnostic data are displayed as visible characters showing the name of an illness, waveforms or pictures on the mobile phone display monitor, and are audible as sounds through a speaker which is also provided in the mobile phone.

Using this apparatus, one can check one's physical condition by the diagnosis made available in this manner. Besides, one can store the periodically collected diagnostic data and send them to the physician at a hospital for the physician's diagnosis without visiting the hospital.

Advantageous Effects

By the present invention, the mobile phone is added with a function of diagnosing a person's illness, by which the name of a person's illness is automatically displayed on the monitor of a mobile phone through auscultation. Using the mobile phone with a stethoscope, one can not only enjoy the convenient existing function of a mobile phone of communication and data processing, Internet connection for listening music, image and sound processing, games and entertainment, but also use the mobile phone as a stethoscope to check one's physical condition whenever necessary in order to promote one's physical health.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a perspective view illustrating a mobile phone containing an interior stethoscopic microphone according to an embodiment of the present invention;

FIG. 2 is a perspective view illustrating a usage of a mobile phone with a stethoscope in FIG. 1;

FIG. 3 is an illustrative view for displaying a diagnostic result on a monitor of a mobile phone;

FIG. 4 is a schematic view of the circuits of the stethoscopic system embedded in a body of a mobile phone;

FIG. 5 is a perspective view illustrating a mobile phone which contains an exterior stethoscopic microphone according to another embodiment of the present invention; and FIG. 6 is an illustrative view showing both auscultating and monitoring.

BEST MODE FOR CARRYING OUT THE INVENTION

The preferred embodiments of the present invention will be explained in detail with reference to the accompanying drawings.

(First Embodiment)

FIG. 1 is a perspective view showing a mobile phone which contains an interior stethoscopic microphone according to an embodiment of the present invention. As shown in this drawing, a small-sized high-performance stethoscopic microphone 3 is embedded in the front surface of a cover 2 of a mobile phone 1, and the stethoscopic microphone 3 is connected to a stethoscopic system that is embedded in a body 1a. An operating switch sw for operating the stethoscopic microphone 3 is arranged at a side of the body 1a.

FIG. 4 is a schematic view of a stethoscopic system embedded in a body of a mobile phone. As shown in this drawing, the stethoscopic system (IC) is embedded as a customized chip in the body 1a of the mobile phone 1, wherein the stethoscopic system includes a filter unit for filtering various noises which are mixed with an auscultated sound collected by the stethoscopic microphone 3, an amplifier unit for amplifying the filtered auscultated sound signals, an A/D converter unit, a standard digital data storage unit which stores standardized digital auscultating sounds by symptom of illness, an information search/comparison unit, a diagnostic data storage unit, and a diagnostic data output unit. The diagnostic data, which shows the result of the auscultation identifying the illness of a patient, is shown on a display monitor 2a which is arranged on the cover 2 of the mobile phone 1, and is audible through a speaker which is arranged in the mobile phone 1.

In the first embodiment of the present invention, a detailed description of the inherent function and usage of the mobile phone communication will be omitted because it is a known art.

FIG. 2 is a view illustrating a usage of a mobile phone with a stethoscope in FIG. 1. The mobile phone with a stethoscope of a new function according to the present invention will be explained as follows. As shown in this drawing, a user turns ON the operating switch sw of the mobile phone 1, and then the user contacts for auscultation the stethoscopic microphone embedded in the cover 2 onto a medical examination part of a human body. When an auscultation is performed, various auscultated sounds such as a heart pulsation, a hematocele, and the like, are collected by the stethoscopic microphone. Since the collected auscultated sounds are mixed with contact-sounds generated when the stethoscopic microphone is contacted onto the human body, and various noises absorbed from the surroundings, the noises are filtered by a filter unit. Then, the analog data of the filtered auscultated sound are amplified by the amplifier unit, and then are converted into digitalized auscultated sound data by the A/D converter unit. Subsequently, when the converted digital auscultated sound data are inputted into the search/comparison unit, they search the pre-stored standardized digital auscultating sound data by symptoms of illness to identify their equivalent in the pre-stored standard sound data, the converted digital auscultated sound data being compared with the searched data. If, as a result of the search and comparison operation, the converted digital auscultated sound data locates its identical or equivalent sound data of the symptoms of illness in the standardized digital sound data within allowable errors, the data is stored as a diagnostic data and outputted through the output unit.

FIG. 3 illustrates how auscultation and outputting of data are done with a mobile phone with a stethoscope. With respect to the output of the resultant diagnostic data, as shown in this drawing, when the user opens the cover 2 of the mobile phone 1, the diagnostic data are displayed with a date of the diagnosis made on the display monitor 2a as visible characters showing the name of an illness, waveforms, pictures, etc., the display monitor being arranged on the cover 2. The outputted data are audible as well through a speaker in the mobile phone.

The data may be deleted, and stored by each date. If the diagnostic data is transmitted to a physician at a remote hospital, a remote-controlled medical examination may be accomplished After the use of the mobile phone with a stethoscope, when the operating switch sw is pushed once more, an operation of the stethoscopic system is finished.

(Second Embodiment)

FIG. 5 is a perspective view illustrating a mobile phone containing an exterior stethoscopic microphone according to another embodiment of the present invention. As shown in this drawing, a jack hole H for connecting the stethoscopic microphone 3 is arranged at a side of the same body 1a of the mobile phone 1 as the first embodiment. The jack hole H is formed for connection with a stethoscopic system embedded in the body 1a of the mobile phone 1. A detachable small-sized high-performance stethoscopic microphone 3 is provided with a jack J for insertion into the jack hole H.

FIG. 6 is an illustrative view of both auscultating and monitoring. In a mobile phone with a stethoscope according to another embodiment of the present invention, as shown in the drawing, when the jack J of the stethoscopic microphone 3 is connected to a jack hole H of the stethoscopic microphone 3 which is formed in the body 1a of the mobile phone 1, the stethoscopic system which is embedded in the body 1a of the mobile phone 1 is turned into operation. When the stethoscopic microphone 3 is contacted to a medical examination part of a human body, the auscultation is accomplished. At this time, as the cover 2 of the mobile phone 1 may be opened, the auscultated results are displayed on the display monitor 2a which is arranged onto the cover 2. In this way, both the auscultation and the displaying of the results of the auscultation, namely the diagnostic data, may be accomplished at the same time. Thus, the diagnostic data, which shows the name of the illness, are visibly displayed instantly, and are audible as well.

The process of the auscultated sound data collected by the stethoscopic microphone 3 is the same as the process of the first embodiment of the present invention.

The operation of the process of the asculation is finished with the separation of the jack J of the stethoscopic microphone 3 from the jack hole H.

INDUSTRIAL APPLICABILITY

The present invention may be used in the computer program industry and a mobile phone industry.

The main function of the mobile phone has been a communication function so far, but from now on medical examination data may be exchanged using the communication function of the mobile phone equipped with a stethoscopic function, and thus a use of the mobile phone may expand into a new area of people's physical health. For instance, if a person suffers from an unexpected illness at a remote place far from a hospital, the condition of the patient can be transmitted to a physician and the hospital at a nearest location using the mobile phone with a stethoscope. Thus, as it is possible to request first aid and send a symptom of illness of the patient swiftly in advance, a physician may effectively prepare a treatment for the patient.

Moreover, as the mobile phone with a stethoscope according to the present invention includes a display monitor and a speaker, any person with no medical auscultating knowledge can accomplish a self-diagnosis by auscultation. Besides, both visually handicapped persons and aurally handicapped persons can use the mobile phone with a stethoscope as a medical examination instrument.

In addition, as communication and data processing functions of a mobile phone are compositely incorporated with an auscultating function of a stethoscope, it offers convenient portability, an easy availableness of data and versatility of functions. Thus, the mobile phone with a stethoscope can be used conveniently with increased utility.

The invention claimed is:

1. An apparatus, comprising:
   a mobile phone having a body; and
   a stethoscope microphone configured to be carried by said mobile phone and configured for use in obtaining sounds made by a patient;
   wherein said stethoscope microphone is an interior microphone incorporated into said body of said mobile phone, wherein said mobile phone has a display monitor that displays an identification of an illness obtained through analysis of the sounds obtained by the stethoscope microphone, wherein said body has a cover onto which said display monitor is located, wherein said cover is movable from a closed position in which said display monitor is positioned towards an interior of said body and is hidden from sight from the patient and any other person to an open position in which said display monitor is viewable by the patient, wherein said stethoscope microphone is on an exterior surface of said cover and contacts the patient when obtaining sounds made by the patient for identification of illness and when obtaining sounds made by the patient for identification of illness said cover is in the closed position such that said display monitor is hidden from sight from the patient and any other person.

2. The apparatus as set forth in claim 1, further comprising an exterior stethoscope microphone attachable and detachable to said mobile phone.

3. The apparatus as set forth in claim 2, wherein said body of said mobile phone has a jack receptacle, and wherein said exterior stethoscope microphone has a jack capable of being attached to and detached from said jack receptacle in order to render said exterior stethoscope microphone attachable and detachable to said mobile phone.

4. The apparatus as set forth in claim 1, further comprising a stethoscopic system carried by said mobile phone, wherein said stethoscopic system receives input from said stethoscope microphone, wherein said stethoscopic system has a filter unit for use in filtering input from said stethoscope microphone, and wherein said stethoscopic system has an amplifier unit for amplifying input from said stethoscope microphone.

5. The apparatus as set forth in claim 4, wherein said stethoscopic system has an analog to digital converter for converting analog wave data of input from said stethoscope microphone into digital sound data, wherein said stethoscopic system has a sound storage unit for storing standardized sound data according to symptom of illness, wherein said stethoscopic system has an information search and comparison unit for searching and comparing said digital sound data with and to said standardized sound data for use in identification of an illness, and wherein said stethoscopic system has a storage unit for storing diagnostic data upon identification of the illness.

6. The apparatus as set forth in claim 5, wherein said stethoscopic system has an output unit for outputting said diagnostic data.

7. The apparatus as set forth in claim 5, wherein said diagnostic data is displayed on said display monitor as visible characters showing the name of the illness and wherein said diagnostic data is audible through a speaker of said mobile phone.

8. The apparatus as set forth in claim 5, wherein said diagnostic data is transmitted by said mobile phone to a health care provider.

9. An apparatus for use in obtaining diagnostic data, comprising:
a mobile phone; and
a stethoscopic system carried by said mobile phone and configured to receive auscultated sound from a patient and to evaluate the auscultated sound in order to identify an illness;
wherein said stethoscopic system has an analog to digital converter unit for converting analog wave data of the auscultated sound into digital auscultated sound data, wherein said stethoscopic system has an auscultating sound storage unit for storage of standardized auscultating sound data by symptom of illness, wherein said stethoscopic system has an information search and comparison unit for searching and comparing the digital auscultated sound data with and to the standardized auscultating sound data for identification of an illness;
wherein a sound waveform and a name of the identified illness are simultaneously displayed on a display monitor of said mobile phone;
wherein said stethoscopic system has a stethoscope microphone to obtain auscultated sound from a patient, wherein said stethoscope microphone has a jack capable of being attached to and detached from a jack receptacle of said mobile phone, and wherein attachment of said jack to said jack receptacle induces said stethoscopic system to begin operation to evaluate the auscultated sound;
wherein said stethoscopic system has a second stethoscope microphone that is carried by said mobile phone and is not detachable from said mobile phone;
wherein said mobile phone has a body that has a cover onto which said display monitor is located, wherein said cover is movable from a closed position in which said display monitor is positioned towards an interior of said body and is hidden from sight from the patient and any other person to an open position in which said display monitor is viewable by the patient, wherein said second stethoscope microphone is on an exterior surface of said cover and contacts the patient when obtaining sounds made by the patient for identification of illness and when obtaining sounds made by the patient for identification of illness with said second stethoscope microphone said cover is in the closed position such that said display monitor is hidden from sight from the patient and any other person.

10. The apparatus as set forth in claim 9, wherein said stethoscopic system has a filter unit for use in filtering the auscultated sound, and wherein said stethoscopic system has an amplifier unit for amplifying the auscultated sound after filtering.

11. The apparatus as set forth in claim 9, wherein said stethoscopic system produces diagnostic data during evaluation of the auscultated sound, and wherein said stethoscopic system has a storage unit for use in storing diagnostic data relating to identification of an illness.

12. The apparatus as set forth in claim 9, wherein said stethoscopic system has an output unit for outputting information relating to an identified illness.

13. The apparatus as set forth in claim 9, wherein diagnostic data of said stethoscopic system is transmitted by said mobile phone to a health care provider in order to inform the health care provider of a condition of a patient.

14. The apparatus as set forth in claim 9, wherein diagnostic data obtained by said stethoscopic system is communicated to a user by a manner selected from the group consisting of alpha numeric characters showing the name of an illness on a display monitor of said mobile phone, waveforms showing the auscultated sound displayed on said display monitor of said mobile phone, pictures on said display monitor of said mobile phone, and audible message through a speaker of said mobile phone.

15. An apparatus, comprising:
a mobile phone; and
a stethoscopic system carried by said mobile phone, wherein said stethoscopic system has a stethoscope microphone for use in obtaining auscultated sound from a patient, and wherein said stethoscopic system has an analog to digital converter for converting analog wave data of the auscultated sound into digital sound data, wherein said stethoscopic system has a sound storage unit for storing standardized sound data according to symptom of illness, wherein said stethoscopic system has an information search and comparison unit for searching and comparing said digital sound data with and to said standardized sound data for use in identification of an illness, wherein said stethoscopic system is configured for displaying the illness on a display monitor of said mobile phone;
wherein said mobile phone is capable of transmitting the illness identified by said stethoscopic system to a health care provider;
wherein said stethoscope microphone is an interior microphone incorporated into a body of said mobile phone, wherein said mobile phone has a body that has a cover onto which said display monitor is located, wherein said cover is movable from a closed position in which said display monitor is positioned towards an interior of said body and is hidden from sight from the patient and any other person to an open position in which said display monitor is viewable by the patient, wherein said stethoscope microphone is on an exterior surface of said cover and contacts the patient when obtaining sounds made by the patient for identification of illness and when obtaining sounds made by the patient for identification of illness said cover is in the closed position such that said display monitor is hidden from sight from the patient and any other person.

* * * * *